(12) United States Patent
Quagliato et al.

(10) Patent No.: US 7,582,667 B2
(45) Date of Patent: Sep. 1, 2009

(54) DIHYDROSPIRO[DIBENZO[A,D][7] ANNULENE-5,4'-IMIDAZOL] COMPOUNDS FOR THE INHIBITION OF BETA-SECRETASE

(75) Inventors: Dominick Anthony Quagliato, Bridgewater, NJ (US); Patrick Michael Andrae, Jamesburg, NJ (US); Yi Fan, Robbinsville, NJ (US)

(73) Assignee: Wyeth, Madison, NJ (US)

( * ) Notice: Subject to any disclaimer, the term of this patent is extended or adjusted under 35 U.S.C. 154(b) by 160 days.

(21) Appl. No.: 11/710,666

(22) Filed: Feb. 23, 2007

(65) Prior Publication Data

US 2007/0203116 A1 Aug. 30, 2007

Related U.S. Application Data

(60) Provisional application No. 60/776,361, filed on Feb. 24, 2006.

(51) Int. Cl.
*A01N 43/50* (2006.01)
*C07D 233/00* (2006.01)
(52) U.S. Cl. .................................. 514/386; 548/301.1
(58) Field of Classification Search ........................ None
See application file for complete search history.

(56) References Cited

U.S. PATENT DOCUMENTS

| | | | |
|---|---|---|---|
| 4,140,793 | A | 2/1979 | Ward |
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0160828 | A1 | 7/2006 | Malamas et al. |
| 2006/0173049 | A1 | 8/2006 | Malamas et al. |
| 2006/0183790 | A1 | 8/2006 | Cole et al. |
| 2006/0183792 | A1 | 8/2006 | Fobare et al. |
| 2007/0004730 | A1 | 1/2007 | Zhou |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0191431 | A1 | 8/2007 | Zhou |
| 2008/0051390 | A1 | 2/2008 | Malamas et al. |

FOREIGN PATENT DOCUMENTS

| | | |
|---|---|---|
| EP | 0861831 A1 | 9/1998 |
| GB | 2013192 A | 8/1979 |
| WO | WO 97/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2004/058727 A1 | 7/2004 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 | 1/2007 |
| WO | WO 2007/016012 A2 | 2/2007 |

OTHER PUBLICATIONS

Cumming et al., Bioorg. & Med. Chem. Lett. 18(2008), 3236-3241.*
Allimony et al., "Synthesis and antimicrobial activity of some nitrogen heterobicyclic systems: Part I", Indian Journal of Chemistry, 1999, vol. 38B, pp. 445-451.
Fact Sheet Alzheimer's Association, 2006.
Lefrance-Jullien et al., "Design and characterization of a new cell-permeant inhibitor of the beta-secretase BACE1", British Journal of Pharmacology, 2005, vol. 145, pp. 228-235.
Lyketsos et al., "Position statement of the American Association for Geriatric Psychiatry regarding principles of care for patients with dementia resulting from Alzheimer's Disease", 2006, vol. 14, pp. 561-573.
Alzheimer'Disease, retrieved from internet on Jun. 27, 2007, http://www.mayoclinic.com/health/alzheimers-disease/DA00161/DSECTION-3.
National Institute of Neurological Discorders and Stroke, "Alzheimer's Disease Information Page", retrieved from internet on Jun. 27, 2007, http://www.ninds.nih.gov/disorders/alzheimersdisease/alzheimersdisease.htm.
PCT Preliminary Report on Patentability, Written Opinion of the ISR, International Patent Application PCT/US2006/024793, International filing date Jun. 26, 2006.

(Continued)

*Primary Examiner*—Golam M. M. Shameem
*Assistant Examiner*—Sun Jae Y Loewe
(74) *Attorney, Agent, or Firm*—Ram W. Sabnis; Scott K. Larsen

(57) ABSTRACT

The present invention provides a 10,11-dihydrospiro[dibenzo [a,d][7]annulene -5,4'-imidazol]-5'(1'H)-one compound of formula I

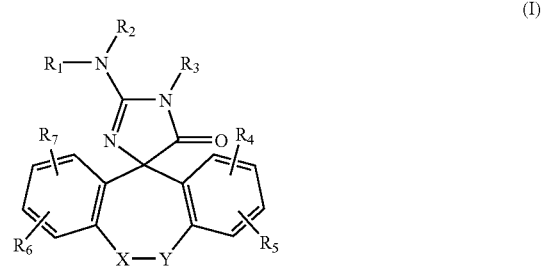

(I)

Also provided are methods and compositions for the inhibition of β-secretase (BACE) and the treatment of β-amyloid deposits and neurofibrillary tangles.

11 Claims, No Drawings

OTHER PUBLICATIONS

PCT Preliminary Report on Patentability, Written Opinion of the ISR, International Patent Application PCT/US2006/024912, International filing date Jun. 26, 2006.

Selkoe, "Alzheimer's Disease: Genes, Proteins, and Therapy", Physiological Reviews, 2001, vol. 81(2), pp. 741-766.

Su et al. "Drug delivery across the blood-brain barrier: why is it difficult? How to measure and improve it?", Expert Opinion on Drug Delivery, Abstract, 2006, vol. 3, pp. 419-425.

Vandana et al., "Transferring coupled liposomes as drug delivery carriers for brain trageting of 5-florouracil", Journal of Drug Targeting, Abstract, 2005, vol. 13 pp. 245-250.

Varghese et al., "Human beta-secretase (BACE) and BACE Inhibitors", J. Med. Chem. 2003, vol. 46(22). pp. 4625-4630.

Tao, Bin and Timberlake, Jack W., Synthesis, 2000, No. 10, 1449-1453.

Xiao, Zejun and Timberlake, Jack W., Journal of Heterocyclic Chemistry, 2000, 37, 773-777.

\* cited by examiner

DIHYDROSPIRO[DIBENZO[A,D][7]ANNULENE-5,4'-IMIDAZOL] COMPOUNDS FOR THE INHIBITION OF BETA-SECRETASE

This application claims the benefit under 35 U.S.C. §119 (e) to co-pending U.S. provisional application No. 60/776,361, filed Feb. 24, 2006, which is hereby incorporated by reference in its entirety.

BACKGROUND OF THE INVENTION

β-Amyloid deposits and neurofibrillary tangles are two major pathologic characterizations associated with Alzheimer's disease (AD). Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630).

β-Amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al, Nature, 1999, 402, 537-540), and studies indicate that the inhibition of BACE inhibits the production of Aβ peptide (Roberds, S. L., et al, Human Molecular Genetics, 2001, 10, 1317-1324).

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the activity of the β-secretase enzyme.

These and other objects and features of the invention will become more apparent by the detailed description set forth hereinbelow.

SUMMARY OF THE INVENTION

The present invention provides a compound of formula I

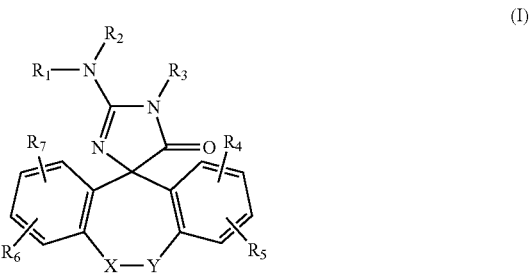

wherein
X is $CH_2$, NH, O or S;
Y is $CH_2$, NH, O or S with the proviso that at least one of X and Y is $CH_2$;
$R_1$ and $R_2$ are each independently H, $COR_8$, $CO_2R_9$ or an optionally substituted alkyl group or $R_1$ and $R_2$ may be taken together with the atom to which they are attached form an optionally substituted 5- to 7-membered ring optionally interrupted by an additional heteroatom selected from O, N or S;
$R_3$ is H, $OR_{10}$ or an alkyl, haloalkyl, alkenyl, alkynyl, cycloalkyl or arylalkyl group each optionally substituted;
$R_4$ and $R_5$ are each independently H, halogen, $NO_2$, CN, $OR_{11}$, $COR_{12}$, $CO_2R_{13}$, $CONR_{14}R_{15}$, $NR_{16}R_{17}$, $NR_{18}COR_{19}$, $NR_{20}SO_2R_{21}$, $SO_2NR_{22}R_{23}$, $SO_nR_{24}$ or an alkyl, alkenyl, alkynyl, cycloalkyl, cycloheteroalkyl, aryl or heteroaryl group each optionally substituted or when attached to adjacent carbon atoms $R_4$ and $R_5$ may be taken together with the atoms to which they are attached to form an optionally substituted 5- to 7-membered ring optionally interrupted by one, two or three heteroatoms selected from O, N or S;
$R_6$ and $R_7$ are each independently H, halogen, CN, $OR_{25}$, $NR_{26}R_{27}$ or an alkyl, alkenyl, alkynyl cycloalkyl, cycloheteroalkyl, aryl or heteroaryl group each optionally substituted;
n is 0, 1 or 2;
$R_8$, $R_9$, $R_{10}$, $R_{11}$, $R_{12}$, $R_{13}$, $R_{19}$ and $R_{25}$ are each independently H or an alkyl, haloalkyl, alkenyl, alkynyl cycloalkyl or aryl group each optionally substituted;
$R_{14}$, $R_{15}$, $R_{16}$, $R_{17}$, $R_{22}$, $R_{23}$, $R_{26}$ and $R_{27}$ are each independently H, $OR_{11}$, $COR_{12}$, $CO_2R_{13}$ or an alkyl, alkenyl, alkynyl cycloalkyl, cycloheteroalkyl, aryl or heteroaryl group each optionally substituted or $R_{14}$ and $R_{15}$ or $R_{16}$ and $R_{17}$ or $R_{22}$ and $R_{23}$ or $R_{26}$ and $R_{27}$ may be taken together with the atom to which they are attached to form an optionally substituted 5- to 7-membered ring optionally interrupted by an additional heteroatom selected from O, N or S;
$R_{18}$ and $R_{20}$ are each independently H, $OR_{11}$, $COR_{12}$, $CO_2R_{13}$ or an alkyl, alkenyl, alkynyl cycloalkyl, cycloheteroalkyl, aryl or heteroaryl group each optionally substituted; and
$R_{21}$ and $R_{24}$ are each independently an alkyl, alkenyl, alkynyl, cycloalkyl, cycloheteroalkyl, aryl or heteroaryl group each optionally substituted; or a tautomer thereof, a stereoisomer thereof or a pharmaceutically acceptable salt thereof.

The present invention also relates to the use 10,11-dihydrospiro[dibenzo -[a,d][7]annulene-5,4'-imidazol]-5'(1'H)-one compounds for the treatment of β-amyloid deposits and neurofibrillary tangles. These compounds are particularly useful in treating Alzheimer's disease, cognitive impairment, Down's Syndrome, HCHWA-D, cognitive decline, senile dementia, cerebral amyloid angiopathy, degenerative dementia, or other neurodegenerative disorders.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deterioration and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21; 4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type and other neurodegenerative and dementia-inducing disorders. Over expression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al, Nature, 1999, 402, 537). BACE1 is a membrane-bound aspartic protease with all the known functional properties and characteristics of β-secretase. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that 10,11-dihydrospiro[dibenzo[a,d][7]-annulene-5,4'-imidazol]-5'(1'H)-one compounds of formula I demonstrate inhibition of β-secretase and the selective inhibition of BACE1. Advantageously, said dibenzoannulene-imidazol compounds may be used as effective therapeutic agents for the treatment, prevention or amelioration of a disease or disorder characterized by elevated β-amyloid deposits or β-amyloid levels in a patient. Accordingly, the present invention provides a dihydrospiro [dibenzo[a,d][7]annulene-5,4'-imidazol] compound of formula I

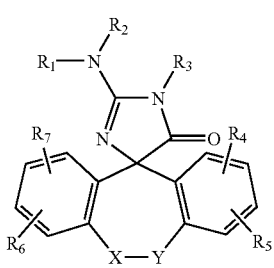

(I)

wherein
X is $CH_2$, NH, O or S;
Y is $CH_2$, NH, O or S with the proviso that at least one of X and Y is $CH_2$;
$R_1$ and $R_2$ are each independently H, $COR_8$, $CO_2R_9$ or an optionally substituted alkyl group or $R_1$ and $R_2$ may be taken together with the atom to which they are attached form an optionally substituted 5- to 7-membered ring optionally interrupted by an additional heteroatom selected from O, N or S;
$R_3$ is H, $OR_{10}$ or an alkyl, haloalkyl, alkenyl, alkynyl, cycloalkyl or arylalkyl group each optionally substituted;
$R_4$ and $R_5$ are each independently H, halogen, $NO_2$, CN, $OR_{11}$, $COR_{12}$, $CO_2R_{13}$, $CONR_{14}R_{15}$, $NR_{16}R_{17}$, $NR_{18}COR_{19}$, $NR_{20}SO_2R_{21}$, $SO_2NR_{22}R_{23}$, $SO_nR_{24}$ or an alkyl, alkenyl, alkynyl, cycloalkyl, cycloheteroalkyl, aryl or heteroaryl group each optionally substituted or when attached to adjacent carbon atoms $R_4$ and $R_5$ may be taken together with the atoms to which they are attached to form an optionally substituted 5- to 7-membered ring optionally interrupted by one, two or three heteroatoms selected from O, N or S;
$R_6$ and $R_7$ are each independently H, halogen, CN, $OR_{25}$, $NR_{26}R_{27}$ or an alkyl, alkenyl, alkynyl cycloalkyl, cycloheteroalkyl, aryl or heteroaryl group each optionally substituted;
n is 0, 1 or 2;
$R_8$, $R_9$, $R_{10}$, $R_{11}$, $R_{12}$, $R_{13}$, $R_{19}$ and $R_{25}$ are each independently H or an alkyl, haloalkyl, alkenyl, alkynyl cycloalkyl or aryl group each optionally substituted;
$R_{14}$, $R_{15}$, $R_{16}$, $R_{17}$, $R_{22}$, $R_{23}$, $R_{26}$ and $R_{27}$ are each independently H, $OR_{11}$, $COR_{12}$, $CO_2R_{13}$ or an alkyl, alkenyl, alkynyl cycloalkyl, cycloheteroalkyl, aryl or heteroaryl group each optionally substituted or $R_{14}$ and $R_{15}$ or $R_{16}$ and $R_{17}$ or $R_{22}$ and $R_{23}$ or $R_{26}$ and $R_{27}$ may be taken together with the atom to which they are attached to form an optionally substituted 5- to 7-membered ring optionally interrupted by an additional heteroatom selected from O, N or S;
$R_{18}$ and $R_{20}$ are each independently H, $OR_{11}$, $COR_{12}$, $CO_2R_{13}$ or an alkyl, alkenyl, alkynyl cycloalkyl, cycloheteroalkyl, aryl or heteroaryl group each optionally substituted, and
$R_{21}$ and $R_{24}$ are each independently an alkyl, alkenyl, alkynyl, cycloalkyl, cyclohetereoalkyl, aryl or heteroaryl group each optionally substituted; or a tautomer thereof, a stereoisomer thereof or a pharmaceutically acceptable salt thereof.

In one embodiment, $R_7$ is an optionally substituted heteroaryl group. Representative heteroaryl groups include pyridine, thiophene, thiazole, thiadiazole, furan, oxazole, oxadiazole, pyrrole, pyrazole, imidazole, triazole, oxathiole, isoxazole, oxazole, oxatriazole, dioxazole, oxathiazole, tetrazole, pyridazine, pyrimidine, pyrazine, triazine, oxazine, oxathiazine, or oxadiazine. The heteroaryl group may be unsubstituted or substituted with alkyl, alkoxy, trifluoroalkyl, trifluoroalkoxy, amino, halogen, hydroxyl, or CN, or forms an N-oxide. For example $R_7$ may be an optionally substituted pyridine or pyrimidine group.

In another embodiment, $R_7$ is a phenyl group optionally substituted with CN, alkoxy, haloalkoxy or halogen.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X' is NR', O or S; and R' is H or an optional substituent as described hereinbelow:

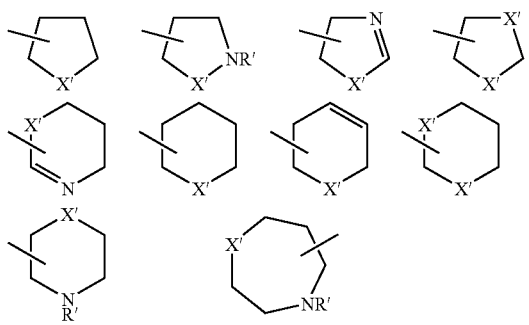

Similarly, as used in the specification and claims, the term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different. Preferably the term haloalkyl designates $CF_3$ and the term haloalkoxy designates $OCF_3$.

In the specification and claims, when the terms alkyl, alkenyl, alkynyl, cycloalkyl, cycloheteroalkyl, aryl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more tautomers. One skilled in the art will recognize that compounds of formula I may also exist as the tautomer (It) as shown below.

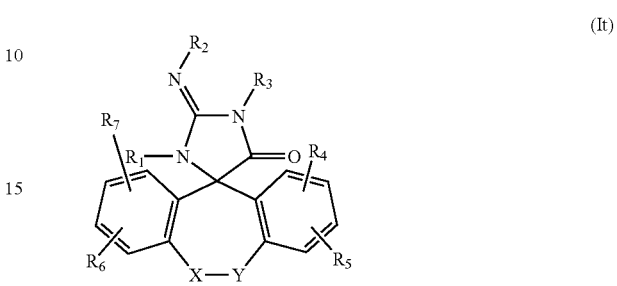

Tautomers often exist in equilibrium with each other. As these tautomers interconvert under environmental and physiological conditions, they provide the same useful biological effects. The present invention includes mixtures of such tautomers as well as the individual tautomers of Formula I and Formula It.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, preferably less than about 50%, more preferably less than about 75%, and even more preferably less than about 90%.

Preferred compounds of the invention are those compounds of formula I wherein X is $CH_2$. Another group of preferred compounds are those compounds of formula I wherein $R_6$ is H or halogen. A further group of preferred compounds are those formula I compounds wherein $R_1$ and $R_2$ are H.

More preferred compounds of the invention are those compounds of formula I wherein X and Y are $CH_2$. Another group of more preferred compounds is those compounds of formula I wherein X and Y are $CH_2$; $R_3$ is alkyl; and $R_7$ is an optionally substituted phenyl or heteroaryl group. A further group of more preferred compounds are those compounds of formula I wherein X and Y are $CH_2$; $R_1$ and $R_2$ are H; $R_3$ is alkyl; $R_4$ is H or fluorine; $R_7$ is an optionally substituted phenyl or heteroaryl group; and $R_7$ is attached in the 7-position.

Preferred compounds of the invention include:
2'-amino-2-methoxy-1'-methyl-7-bromo-10,11-dihydrospiro[dibenzo[a,d][7]-annulene-5,4'-imidazol]-5'(1'H)-one;
2'-amino-2-methoxy-1'-methyl-7-bromo-10,11-dihydrospiro[dibenzo[a,d][7]annulene-5,4'-imidazol]-5'(1'H)-one;

2'-amino-2-methoxy-1,1'-dimethyl-7-pyridin-3-yl-10,11-dihydrospiro[dibenzo[a,d][7]annulene-5,4'-imidazol]-5' (1'H)-one;

2'-amino-7-(2-fluoropyridin-3-yl)-2-methoxy-1,1'-dimethyl-10,11-dihydrospiro[dibenzo[a,d][7]annulene-5,4'-imidazol]-5'(1'H)-one;

2'-amino-2-methoxy-1,1'-dimethyl-7-pyrimidin-5-yl-10,11-dihydrospiro[dibenzo[a,d][7]annulene-5,4'-imidazol]-5' (1'H)-one;

2'-amino-7-(6-fluoropyridin-3-yl)-2-methoxy-1,1'-dimethyl-10,11-dihydrospiro[dibenzo[a,d][7]annulene-5,4'-imidazol]-5'(1'H)-one;

2'-amino-7-(2,5-difluorophenyl)-2-methoxy-1,1'-dimethyl-10,11-dihydrospiro[dibenzo[a,d][7]annulene-5,4'-imidazol]-5'(1'H)-one;

3-(2'-amino-8-methoxy-1',9-dimethyl-5'-oxo-1',5', 10,11-tetrahydrospiro[dibenzo[a,d][7]annulene-5,4'-imidazol]-3-yl)benzonitrile;

2'-amino-2-methoxy-7-(3-methoxyphenyl)-1,1'-dimethyl-10,11-dihydrospiro[dibenzo[a,d][7]annulene-5,4'-imidazol]-5'(1'H)-one;

2'-amino-7-(3,5-difluorophenyl)-2-methoxy-1,1'-dimethyl-10,11-dihydrospiro[dibenzo[a,d][7]annulene-5,4'-imidazol]-5'(1'H)-one;

(5S)-2'-amino-2-methoxy-1,1'-dimethyl-7-pyrimidin-5-yl-10,11-dihydrospiro[dibenzo[a,d][7]annulene-5,4'-imidazol]-5'(1'H)-one;

(5R)-2'-amino-2-methoxy-1,1'-dimethyl-7-pyrimidin-5-yl-10,11-dihydrospiro[dibenzo[a,d][7]annulene-5,4'-imidazol]-5'(1'H)-one;

2'-amino-2-methoxy-1'-methyl-7-phenyl-10,11-dihydrospiro[dibenzo[a,d][7]annulene-5,4'-imidazol]-5'(1'H)-one;

or a tautomer thereof or a stereoisomer thereof or a pharmaceutically acceptable salt thereof.

Compounds of the invention may be conveniently prepared using conventional synthetic methods and, if required, standard separation and isolation techniques. For example, compounds of formula I wherein X and Y are $CH_2$; $R_1$ and $R_2$ are H; and $R_7$ is other than aryl or heteroaryl (Ia) may be prepared by reacting a bromomethylbenzoate of formula II with triphenylphosphine to give the corresponding phosphonium bromide of formula III; reacting said formula III bromide with a benzaldehyde of formula IV to give the vinyl compound of formula V; reducing said formula IV compound using standard reduction techniques such as catalytic hydrogenation and hydrolyzing the reduced compound to give the benzoic acid of formula VI; reducing the formula VI acid using conventional reducing agents such as $LiBH_4$ and chlorotrimethylsilane (TMS-Cl) to give the corresponding phenylmethanol compound of formula VII; reacting the formula VII phenylmethanol with iodine in the presence of triphenylphosphine to give the phenyliodomethane compound of formula VIII; reacting said formula VIII compound with potassium cyanide to give the phenylacetonitrile of formula IX; reacting said formula IX acetonitrile with acetic acid and $H_2SO_4$ to give the phenylacetic acid of formula X; reacting said formula X acid with phosphorous pentoxide to give the cycloocten-5-one compound of formula XI; oxidizing the formula XI compound with selenium dioxide to give the dione of formula XIII; and reacting the formula XII dione with a guanidine of formula XIII to give the desired compound of formula Ia. The reactions are shown in Flow Diagram I wherein Ph represents phenyl.

FLOW DIAGRAM I

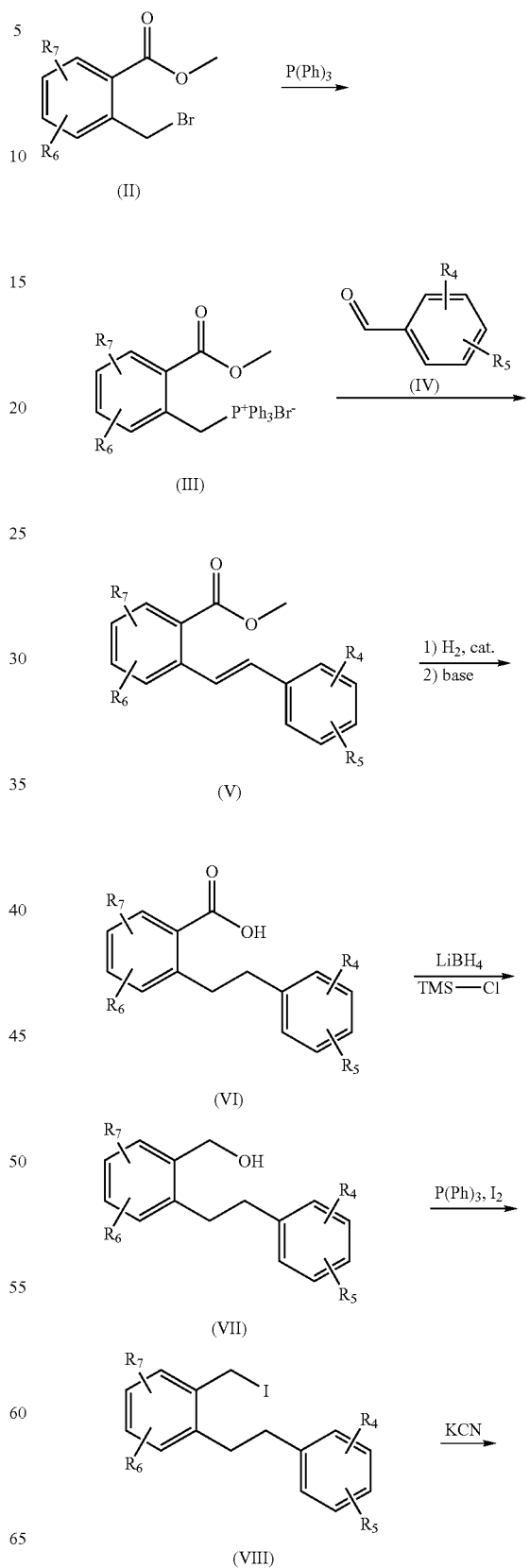

-continued

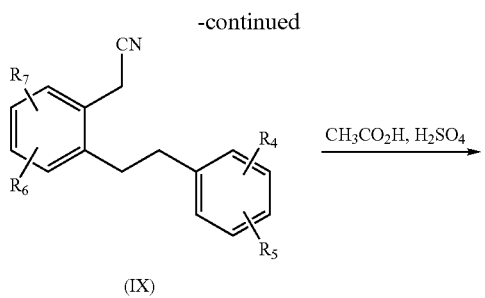

(IX)

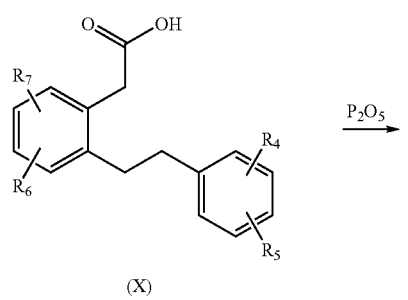

(X)

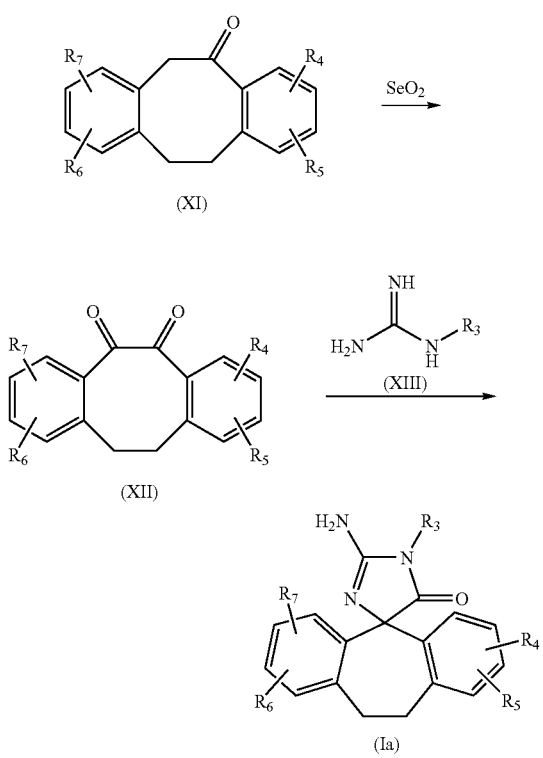

FLOW DIAGRAM II

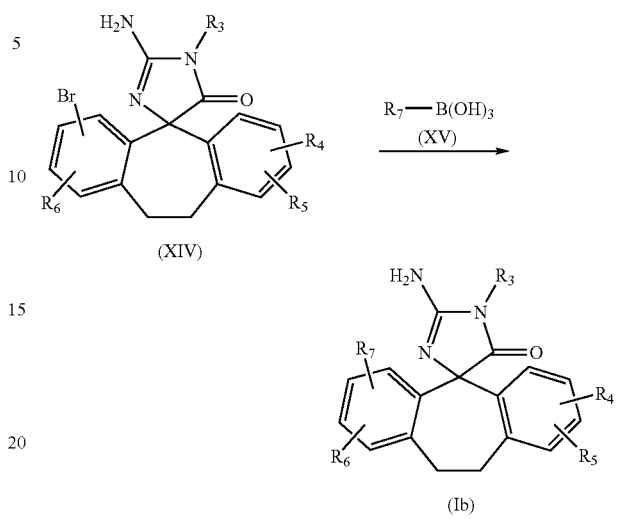

Compounds of formula I wherein X and Y are $CH_2$; $R_1$ and $R_2$ are H; and $R_7$ is aryl or heteroaryl (Ib) may be prepared by reacting a compound of formula XIV with an aryl or heteroaryl boronic acid of formula XV to give the desired compound of formula Ib. The reaction is shown in Flow Diagram II wherein $R_7$ is an optionally substituted aryl or heteroaryl group.

Advantageously, the compounds of formula I act as BACE inhibitors for the treatment or prevention of β-amyloid deposits and neurofibrillary tangles associated with such diseases as Alzheimer's disease, Trisomy 21 (Down's Syndrome), Hereditary Cerebral Hemorrhage with Amyloidosis of the Dutch-type (HCHWA-D), and other neurodegenerative disorders. Accordingly, the present invention provides methods for modulating BACE and treating, preventing, or ameliorating β-amyloid deposits and neurofibrillary tangles associated with diseases and disorders such as Alzheimer's disease, Trisomy 21 (Down's Syndrome), Hereditary Cerebral Hemorrhage with Amyloidosis of the Dutch-type (HCHWA-D), and other neurodegenerative disorders. Such methods generally involve administering to a patient suspected of suffering from or being susceptible to the disease or injury an effective amount of a compound of formula I. Also according to the present invention there is provided a method of treating Alzheimer's disease and related senile dementia's in humans or other mammals which comprises administering to a human or other mammal an effective amount of a compound of the present invention.

The present invention also provides methods for modulating (and, preferably, inhibiting) the activity of BACE, comprising administering to a patient and/or contacting a receptor thereof with an effective amount of at least one compound of Formula I. Certain methods further comprise determining BACE activity, either before or after said contacting step.

The present invention also provides methods of ameliorating β-amyloid deposits in a mammal, comprising administering to said mammal an effective amount of at least one compound of Formula I. Further methods ameliorate neurofibrillary tangles in a mammal, and comprise administering to said mammal an effective amount of at least one compound of Formula I.

Also provided are methods of ameliorating symptoms of Alzheimer's disease, cognitive impairment, Down's Syndrome, HCHWA-D, cognitive decline, senile dementia, cerebral amyloid angiopathy, degenerative dementia, or other neurodegenerative disorders in a mammal, comprising administering to said mammal an effective amount of at least one compound of Formula I.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "patient", as used herein, refers to a mammal, preferably a human.

The terms "effective amount", "therapeutically effective amount" and "effective dosage" as used herein, refer to the amount of a compound that, when administered to a patient, is effective to at least partially ameliorate (and, in preferred embodiments, cure) a condition from which the patient is suspected to suffer. It is understood that the effective dosage of the active compounds of this invention may vary depending upon the particular compound utilized, the mode of administration, the condition, and severity thereof, of the condition being treated, as well as the various physical factors related to the individual being treated.

The present invention also provides a pharmaceutical composition which comprises an effective amount of a compound of formula I and a pharmaceutically acceptable carrier.

The term "carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

In certain embodiments, the present invention is directed to prodrugs. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

For a more clear understanding, and in order to illustrate the invention more clearly, specific examples thereof are set forth hereinbelow. The following examples are merely illustrative and are not to be understood as limiting the scope and underlying principles of the invention in any way. Various modifications of the invention, in addition to those described herein, will be apparent to those skilled in the art from the foregoing description. Such modifications are also intended to fall within the scope of the appended claims.

Unless otherwise stated, all parts are parts by weight. The term NMR designates proton nuclear magnetic resonance, and MS is mass spectroscopy with (+) referring to the positive mode which generally gives a M+1 (or M+H) absorption where M=the molecular mass.

EXAMPLE 1

Preparation of 3-Methoxy-2-methylbenzaldehyde

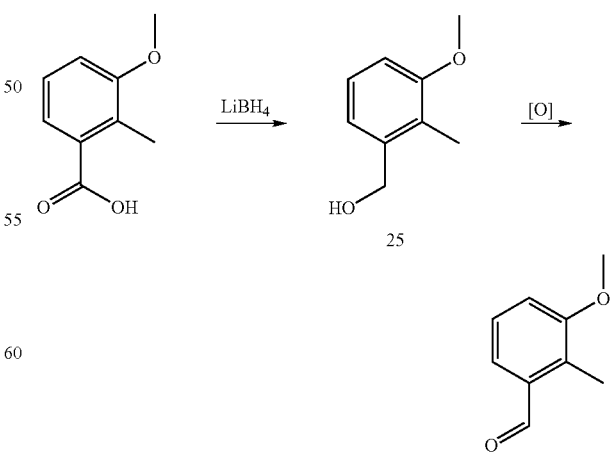

To a stirred mixture of LiBH$_4$ (2.62 g; 120 mmol) in tetrahydrofuran (60 mL) was slowly added, via syringe, chlorotrimethylsilane (30.1 mL; 241 mmol). After stirring for 10 minutes, 3-methoxy-2-methylbenzoic acid (10.0 g, 60 mmol) was added in small portions. The mixture was stirred at ambient temperature for 18 hours. The mixture was cooled in an ice bath and methanol was slowly added until bubbling ceased and the solution turned clear. The reaction solution was evaporated to dryness. The residue was dispersed in dichloromethane and water. The phases were separated. The aqueous phase was basified with NaOH solution to pH 9-10 extracted with dichloromethane. The extracts were combined, dried over MgSO$_4$, and evaporated to give (3-methoxy-2-methylphenyl)methanol 25, 9.10 g, 99% yield.

A stirred suspension of pyridinium chlorochromate (19.2 g; 89.2 mmol) in dichloromethane at ambient temperature was treated with a solution of (3-methoxy-2-methylphenyl) methanol (9.05 g; 59.47 mmol) in dichloromethane. The reaction solution immediately turned a greenish-brown color. The reaction was stirred for 3.5 hr, diluted 50% with diethyl ether and decanted. The brown gummy residue was triturated twice more with diethyl ether (40 mL) and the ether extracts were combined and evaporated to yield a yellow oil. The oil was passed through a column of silica gel with an ether/hexane mixture to yield the title product, 8.74 g; 97% yield.

EXAMPLE 2

Preparation of 2'-Amino-2-methoxy-1'-methyl-7-bromo-10,11-dihydrospiro[dibenzo[a,d][7]annulene-5,4'-imidazol]-5'(1'H)-one

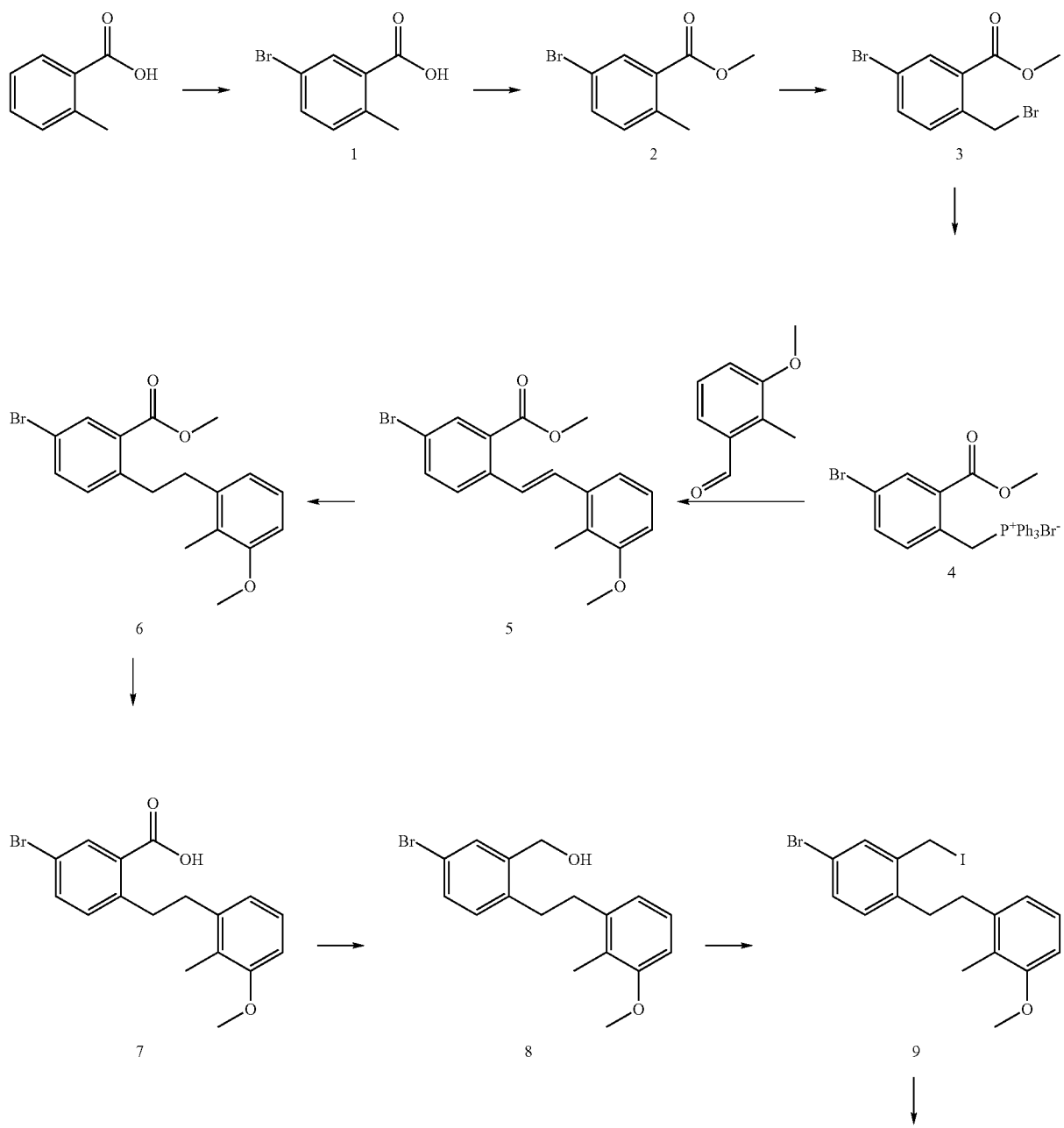

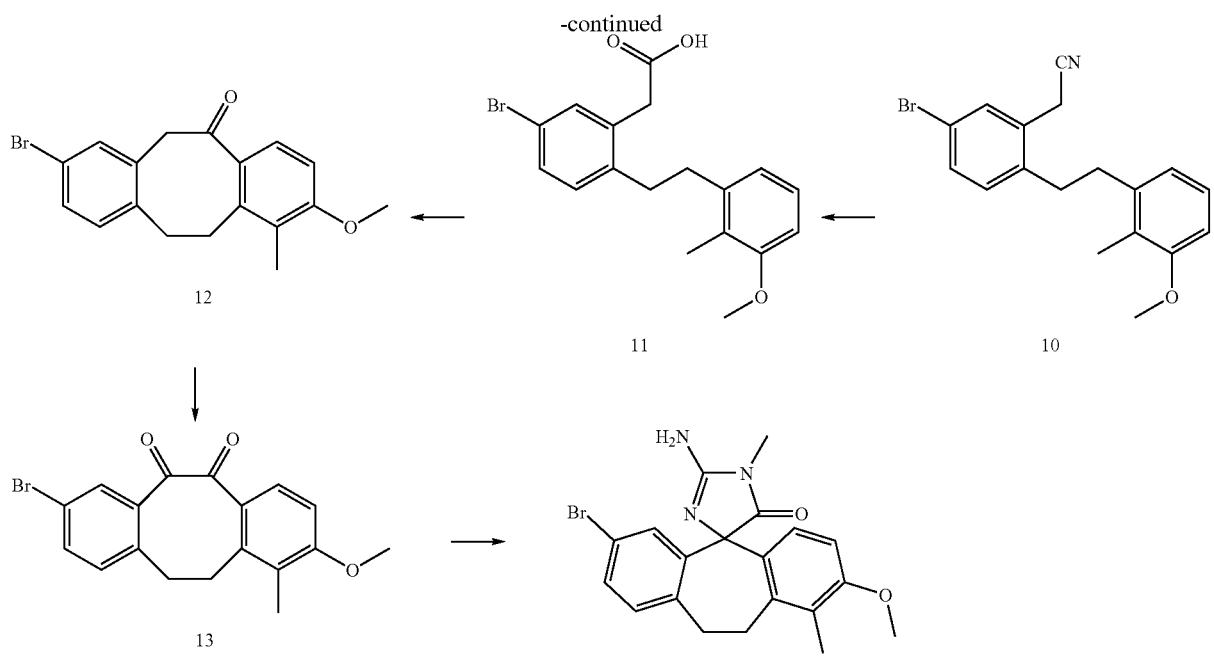

5-Bromo-2-methylbenzoic acid (1)

To 1.10 g of iron filings was added 20 mL of bromine. The mixture was cooled to 0° C. and 40.0 g of solid o-toluic acid was added over 10 minutes. Stirring was continued until the mixture became firm. The residue was allowed to stand at room temperature for 16 hours. The solid was crushed to a fine powder and washed with water. The solid was filtered from the water and again crushed, washed, and dried thoroughly to obtain 60.8 g (96%) of a pink powder that consists of a mixture of the title compound and 3-bromo-2-methylbenzoic acid (40% of the mixture by LC).

5-Bromo-2-methyl-benzoic acid methyl ester (2)

The crude 5-bromo-2-methylbenzoic acid (1) (60.8 g; 283 mmol) was stirred in methanol (400 mL) and concentrated sulfuric acid (6 mL) was added. The mixture was heated at gentle boiling for 20 hours. The solvent was evaporated and the residue was taken up into toluene and water. The solution was shaken and the phases were separated. The organic layer was washed with dilute aqueous $NaHCO_3$, water, and brine. The solution was dried with $MgSO_4$, filtered, and evaporated to get an orange oil. Fractional distillation at reduced pressure yields a mixture of the title compound and 3-bromo-2-methylbenzoic acid methyl ester (47.9 g; 74%).

5-Bromo-2-bromomethyl-benzoic acid methyl ester (3)

The mixture of 3- and 5-bromo-2-methylbenzoic acid methyl ester (35.79 g; 156 mmol) is dissolved in carbon tetrachloride (200 mL). To the solution is added N-bromosuccinimide (29.5 g; 166 mmol), followed by AIBN (54 mg) and the mixture was heated at reflux temperature for 20 hours. Then the mixture was cooled to room temperature and the succinimide was filtered from solution and rinsed with carbon tetrachloride. The solvent was evaporated to yield a mixture of the title compound and 3-bromo-2-bromomethylbenzoic acid methyl ester (48.1 g; crude mass).

(4-Bromo-2-methoxycarbonyl-benzyl)-triphenylphosphonium bromide (4)

The mixture of 3- and 5-bromo-2-bromomethylbenzoic acid methyl ester (48.1 g; 156 mmol) was stirred in 400 mL of acetonitrile with triphenylphosphine (41.0 g, 156 mmol). The solution was heated at reflux temperature for three hours. The solution is cooled to room temperature and the title compound precipitates as a white solid which precipitates is filtered and rinsed with acetonitrile (34.2 g; 38%).

5-Bromo-2-[2-(3-methoxy-2-methylphenyl)-vinyl]-benzoic acid methyl ester (5)

To a stirred mixture of (4-bromo-2-methoxycarbonylbenzyl)-triphenylphosphonium bromide (4) (34.2 g; 60.0 mmol), DBU (1,8-diazabicyclo(5.4.0) undec-5-ene; 20.1 g; 132 mmol), and 3-methoxy-2-methylbenzaldehyde (7.21 g; 48.0 mmol) in acetonitrile were heated at reflux temperature for 2 hours. The mixture was cooled and the solvent was evaporated. The residue was partitioned between water and ethyl acetate and the organic phase was washed with 0.1 N HCl, water, and brine. The solution was dried over $MgSO_4$, filtered, and evaporated. The residue was crystallized from ethyl acetate and hexane to yield compound 5 (14.5 g; 84%).

5-Bromo-2-[2-(3-methoxy-2-methylphenyl)-ethyl]-benzoic acid methyl ester (6)

To 5-bromo-2-[2-(3-methoxy-2-methylphenyl)-vinyl]-benzoic acid methyl ester (5) (4.99 g; 13.8 mmol), stirring in ethyl alcohol (70 mL) and acetic acid (23 mL), was added $PtO_2$ (0.075 g; 2.4%). The solution was stirred in a hydrogen atmosphere (balloon pressure) and the temperature of the solution was raised to 38° C. The reaction was monitored closely by TLC and the mixture was cooled after three hours. The reaction mixture was filtered and evaporated to give compound 6 as a residue. The residue was carried on to the next step without further purification.

5-Bromo-2-[2-(3-methoxy-2-methylphenyl)-ethyl]-benzoic acid (7)

The crude 5-bromo-2-[2-(3-methoxy-2-methylphenyl)-ethyl]-benzoic acid methyl ester 6 was stirred with 50% KOH solution (5 mL), water (30 mL), methanol (12 mL), and THF (30 mL), heated at reflux temperature for three hours and concentrated in vacuo to remove the organic solvents. The resultant aqueous suspension was acidified using 1.0 N HCl solution and filtered. The filtercake was dried over night to give the benzoic acid 7 as a white solid, 4.74 g; 98% yield.

5-Bromo-2-[2-(3-methoxy-2-methylphenyl)-ethyl]-phenylmethanol (8)

Into a dry 100 mL flask was weighed $LiBH_4$ (0.55 g; 25.0 mmol). THF (25 mL) was added and the suspension was cooled to 0° C. To the chilled suspension was added chlorotrimethylsilane (6.36 mL; 50.0 mmol). Then solid 5-bromo-2-[2-(3-methoxy-2-methylphenyl)-ethyl]-benzoic acid 7 (4.37 g; 12.5 mmol) was added portion-wise, slowly enough to control bubbling of the mixture. After addition, the ice bath was removed and the suspension was stirred at ambient temperature overnight. The mixture was quenched by slowly adding methanol until the bubbling stopped and the solution turned clear. The solvents were evaporated and the residue was stirred in water, basified using 2.5 N NaOH solution and extracted with dichloromethane. The organic extracts were combined, dried over $Na_2SO_4$ and evaporated to obtain the compound 8 as a low-melting solid (4.19 g crude).

5-Bromo-2-[2-(3-methoxy-2-methylphenyl)-ethyl]-phenyliodomethane (9)

To polymer-supported triphenylphosphine (9.2 g; ~27.5 mmol) in dichloromethane (40 mL) was added iodine (6.98 g; 27.5 mmol). The mixture was stirred for 30 minutes and then imidazole (1.87 g; 27.5 mmol) was added to the mixture. After stirring for 15 minutes a solution of 5-bromo-2-[2-(3-methoxy-2-methylphenyl)-ethyl]-phenylmethanol 8 (4.19 g; 12.5 mmol) in dichloromethane (100 mL) was added. The mixture was heated at reflux for 2 hours, cooled to room temperature and filtered. The filtrate was washed sequentially with sodium thiosulfate solution, water, and brine, dried over $MgSO_4$, and concentrated to dryness at ambient temperature under high vacuum to give compound 9 as a yellow oil, 5.56 g.

5-Bromo-2-[2-(3-methoxy-2-methyl-phenyl)-ethyl]-phenylacetonitrile (10)

To 5-bromo-2-[2-(3-methoxy-2-methylphenyl)-ethyl]-phenyliodomethane 9 (5.56 g; 12.5 mmol) in dichloromethane (10 mL), isopropyl alcohol (10 mL), and DMSO (3 mL), was added potassium cyanide (1.22 g; 18.8 mmol). The mixture was stirred at 42° C. for 16.5 hours and concentrated in vacuo. The resultant residue was taken up in dichloromethane and water. The solution was shaken and the layers were separated. The organic layer was washed sequentially with water and brine, dried over $MgSO_4$ and concentrated in vacuo to give an amber oil. The oil was chromatographed using $SiO_2$ and hexane/ethyl acetate (3:2) as eluent to give compound 10, 1.99 g; 46% yield.

5-Bromo-2-[2-(3-methoxy-2-methylphenyl)-ethyl]-phenylacetic acid (11)

A stirred mixture of 5-bromo-2-[2-(3-methoxy-2-methylphenyl)-ethyl]-phenylacetonitrile 10 (8.57 g; 24.9 mmol) in water and acetic acid was treated drop-wise with concentrated sulfuric acid (8.5 mL), heated at 115° C. for 5 hours, cooled to ambient temperature, diluted with water and extracted with chloroform. The extracts were combined, dried over $Na_2SO_4$, and evaporated. The resultant residue was purified on a silica gel column (hexane and ethyl acetate (7:3) as eluent) to give compound 11, 5.0 g, 55% yield.

8-Bromo-2-methoxy-1-methyl-11,12-dihydro-6H-dibenzo[a,e]cycloocten-5-one (12)

To a stirred suspension of 5-bromo-2-[2-(3-methoxy-2-methyl-phenyl)-ethyl]-phenylacetic acid (11) (4.38 g; 12.06 mmol) in toluene (20 mL), was added phosphorous pentoxide (6.0 g; 42.2 mmol). The mixture was heated at 90° C. for 16 hours. The mixture was cooled, treated with 1.0 N solution of sodium hydroxide and extracted with chloroform. The extracts were combined, dried over Na2SO4, and evaporated. The resultant residue was chromatoraped on silica gel using hexane and ethyl acetate (4:1) to give compound 12 as colorless crystals, 2.40 g; 55% yield.

8-Bromo-2-methoxy-1-methyl-11,12-dihydro-dibenzo[a,e]cyclooctene-5,6-dione (13)

A mixture of 8-bromo-2-methoxy-1-methyl-11,12-dihydro-6H-dibenzo [a,e]cycloocten-5-one 12 (1.0 g: 2.9 mmol), acetic acid and selenium dioxide (0.64 g; 5.8 mmol) was stirred at 150° C. for 2 hr, cooled to room temperature, diluted with dichloromethane and filtered through silica gel to remove the suspended solids. The filtrate was evaporated to dryness. The residue was heated in ethyl acetate and crystallized by adding hexane to give compound 13 as grey needles, 0.71 g, 68% yield.

2'-Amino-2-methoxy-1'-methyl-7-bromo-10,11-dihydrospiro[dibenzo[a,d][7]-annulene-5,4'-imidazol]-5'(1'H)-one A solution of 8-bromo-2-methoxy-1-methyl-11,12-dihydro-dibenzo[a,e]cyclo-octene-5,6-dione 13 (2.49 g; 6.9 mmol) in dioxane and ethanol was treated with N-methylguanidine (1.52 g, 13.9 mmol), followed by a solution of sodium carbonate (1.47 g; 13.9 mmol) in water, heated at 85° C. for 3 hours, cooled and concentrated in vacuo. The resultant residue was taken up in chloroform and washed with water. The chloroform phase was separated, dried over magnesium sulfate and evaporated. This residue was crystallized from ethyl acetate and hexane to give the title product as a tan powder, 1.62 g (57% yield, identified by NMR and mass spectral analyses.

EXAMPLE 3

Preparation of 2'-Amino-2-methoxy-1,1'-dimethyl-7-pyridin-3-yl-10,11-dihydrospiro[dibenzo[a,d][7]annulene-5,4'-imidazol]-5'(1'H)-one

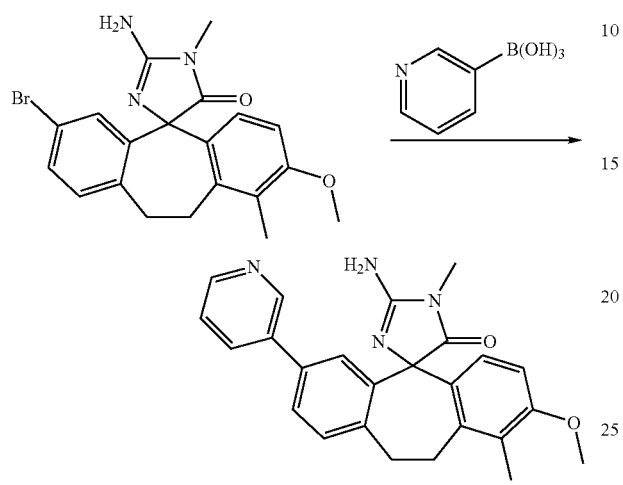

A mixture of 2'-amino-2-methoxy-1'-methyl-7-bromo-10,11-dihydrospiro[dibenzo[a,d][7]annulene-5,4'-imidazol]-5'(1'H)-one (0.130 g; 0.314 mmol), dioxane (5 mL, de-oxygenated), 3-pyridineboronic acid (77.1 mg; 0.628 mmol) and 2.0 N Na$_2$CO$_3$ solution (0.63 mL; 4.0 eq.) was stirred at reflux temperature for one hour, cooled to ambient temperature and concentrated in vacuo. The resultant residue was partitioned in chloroform and water. The organic phase was dried over sodium sulfate, filtered, and evaporated. This residue was purified by HPLC with a Phenomenex CN column using a solvent system consisting of A) hexane and B) dichloromethane/methanol (4:1). A gradient starting at 50% B and increasing to 100% B was used for purification. The purified solid was crystallized from hot ethyl acetate and hexane to yield the title compound as tan crystals, 57 mg (44% yield), mp 235-9° C.; identified by NMR and mass spectral analyses. MS (ES) m/z 413.15 [M+H]+.

EXAMPLES 4-10

Preparation of 2'-Amino-2-methoxy-1,1'-dimethyl-7-heteroaryl- or -aryl-10,11-dihydrospiro[dibenzo[a,d][7]annulene-5,4'-imidazol]-5'(1'H)-one Compounds

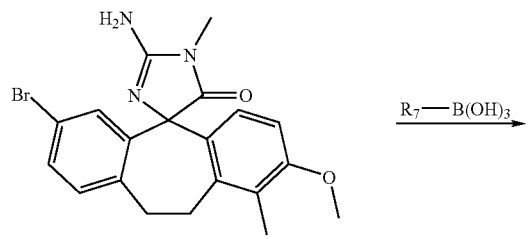

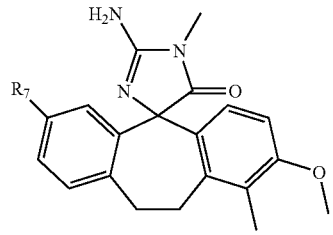

Using essentially the same procedure described in Example 3 and employing the appropriate boronic acid, the compounds shown in Table I were obtained and identified by NMR and mass spectral analyses.

TABLE I

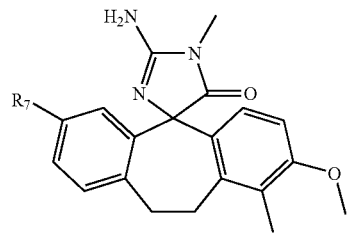

| Ex. No. | R7 | mp ° C. | M + H |
|---|---|---|---|
| 4 | 2-fluoro-3-pyridyl | 153-155 | 431.1 |
| 5 | 5-pyrimidyl | 284-285 | 414.1 |
| 6 | 4-fluoro-3-pyridyl | 251-253 | 429.2 |
| 7 | 2,5-difluorophenyl | 155-195 | 446.1 |
| 8 | 3-cyanophenyl | 269-280 | 437.1 |
| 9 | 3-methoxyphenyl | 138-135 | 442.1 |
| 10 | 3,5-difluorophenyl | 245-249 | 448.1 |

EXAMPLE 11

Preparation of (5S)-2'-amino-2-methoxy-1,1'-dimethyl-7-pyrimidin-5-yl-10,11-dihydrospiro[dibenzo[a,d][7]annulene-5,4'-imidazol]-5'(1'H)-one (A) [WAY-257643] and (5R)-2'-amino-2-methoxy-1,1'-dimethyl-7-pyrimidin-5-yl-10,11-dihydrospiro[dibenzo[a,d][7]annulene-5,4'-imidazol]-5'(1'H)-one (B) [WAY-257644]

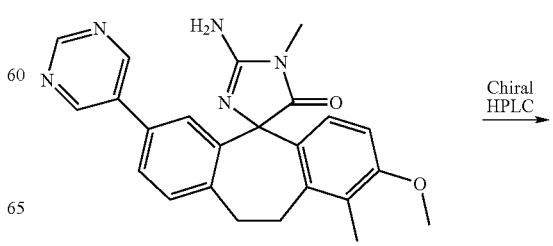

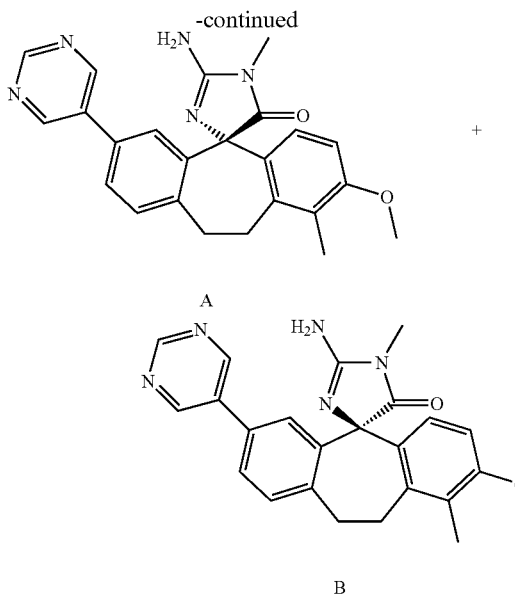

A

B

A racemic mixture of 2'-amino-2-methoxy-1,1'-dimethyl-7-pyrimidin-5-yl-10,11-dihydrospiro[dibenzo[a,d[7]annulene-5,4'-imidazol]-5'(1'H)-one was dissolved in ethanol/methanol/dichloromethane (1/21/1) and placed on a chiral HPLC using a Chiralpak AD column, 2×25 cm with 45% ethyl alcohol in hexane as the mobile phase to give the title enantiomers: A, (5-S) isomer, 84 mg, mp 237-238° C., $[\alpha]_D^{25}=-22.0°$, identified by NMR and mass spectral analyses, MS (ES) m/z 414.2 [M+H]+]; and B, (5-R) isomer, 75 mg, mp 237-238° C.; $[\alpha]_D^{25}=+25.0°$, identified by NMR and mass spectral analyses, MS (ES) m/z 414.2 [M+H]+].

EXAMPLE 12

Preparation of 2'-Amino-2-methoxy-1'-methyl-7-phenyl-10,11-dihydrospiro[dibenzo[a,d][7]annulene-5,4'-imidazol]-5'(1'H)-one (WAY-253340)

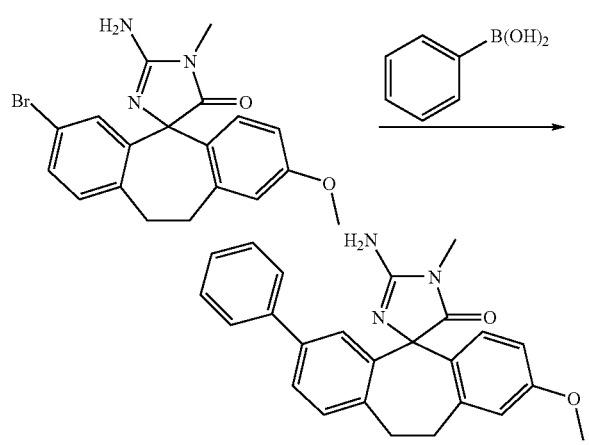

Using essentially the same procedure described in Example 3 and employing 2'-amino-2-methoxy-1'-methyl-7-bromo-10,11-dihydrospiro[dibenzo[a,d][7]annulene-5,4'-imidazol]-5'(1'H)-one and phenylboronic acid, the title compound was obtained as an off-white powder, mp 167-171° C., identified by NMR and mass spectral analyses.

EXAMPLE 13

Evaluation of BACE-1 Binding Affinity of Test Compounds

Fluorescent Kinetic Assay

Final Assay Conditions: 10 nM human BACE1 (or 10 nM Murine BACE1), 25 μM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat. #24, 124-5, CHAPS was from Research Organics, Cat. #1304C 1X, PBS was from Mediatech (Cellgro), Cat#21-031-CV, peptide substrate AbzSEVNLDAEFRDpa was from AnaSpec, Peptide Name: WABC-6

Determination of stock substrate (AbzSEVNLDAEFRDpa) concentration: ~25 mM stock solution is made in DMSO using the peptide weight and MW, and diluted to ~25 μM (1:1000) in 1×PBS. Concentration is determined by absorbance at 354 nm using an extinction coefficient ε of 18172 $M^{-1}cm^{-1}$, the concentration of stock substrate is corrected, and the substrate stock stored in small aliquots in −80° C.

[Substrate Stock]=$ABS^{354\ nm}*10^6/18172$ (in mM)

The extinction coefficient $\epsilon^{354\ nm}$ was adapted from TACE peptide substrate, which had the same quencher-fluorophore pair.

Determination of Stock Enzyme Concentration: the stock concentration of each enzyme is determined by absorbance at 280 nm using ε of 64150 $M^{-1}cm^{-1}$ for hBACE1 and MuBACE1 in 6 M Guanidinium Hydrochloride (from Research Organics, Cat. # 5134G-2), pH ~6. The extinction coefficient $\epsilon^{280\ nm}$ for each enzyme was calculated based on known amino acid composition and published extinction coefficients for Trp (5.69 $M^{-1}\ cm^{-1}$) and Tyr (1.28 $M^{-1}\ cm^{-1}$) residues (*Anal. Biochem.* 182, 319-326).

Dilution and mixing steps: total reaction volume: 100 μL
  2× inhibitor dilutions in buffer A (66.7 mM Na-Acetate, pH 4.5, 0.0667% CHAPS) were prepared,
  4× enzyme dilution in buffer A (66.7 mM Na-Acetate, pH 4.5, 0.0667% CHAPS) were prepared,
  100 μM substrate dilution in 1× PBS was prepared, and
  50 μL 2× Inhibitor, 25 μL 100 μM substrate are added to each well of 96-well plate (from DYNEX Technologies, VWR #: 11311-046), immediately followed by 25 μL 4× enzyme (added to the inhibitor and substrate mix), and the fluorescence readings are initiated.

Fluorescence Readings: Readings at $\lambda_{ex}$ 320 nm and $\lambda_{em}$ 420 nm are taken every 40 sec for 30 min at room temperature and the linear slope for substrate cleavage rate ($v_i$) determined.

Calculation of % Inhibition:

$$\% \text{ Inhibition}=100*(1-v_i/v_0)$$

$v_i$: substrate cleavage rate in the presence of inhibitor
$v_0$: substrate cleavage rate in the absence of inhibitor
$IC_{50}$ Determination:

$$\% \text{ Inhibition}=((B*IC_{50}^n)+(100*I_0^n))/(IC_{50}^n+I_0^n)$$

(Model #39 from LSW Tool Bar in Excel where B is the % inhibition from the enzyme control, which should be close to 0.) % Inhibition is plotted vs. Inhibitor Concentration ($I_0$) and the data fit to the above equation to obtain $IC_{50}$ value and Hill number (n) for each compound. Testing at least 10 different inhibitor concentrations is preferred. The data obtained are shown in Table II below.

TABLE II

| Ex. No. | BACE1 (IC$_{50}$ μM) |
|---|---|
| 3 | 0.077 |
| 4 | 0.063 |
| 5 | 0.060 |
| 6 | 0.108 |
| 7 | 0.250 |
| 8 | 0.235 |
| 9 | 0.138 |
| 10 | 0.376 |
| 11A | 0.378 |
| 11B | 0.071 |
| 12 | 0.180 |

What is claimed is:

1. A compound of formula I

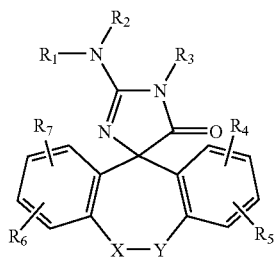

(I)

wherein
X is $CH_2$;
Y is $CH_2$;
$R_1$ and $R_2$ are each independently H, or an optionally substituted alkyl group;
$R_3$ is H or an alky group optionally substituted;
$R_4$ and $R_5$ are each independently H, halogen, $OR_{11}$, or an alkyl, alkenyl, or alkynyl, group optionally substituted;
$R_6$ and $R_7$ are each independently H, halogen, CN, $OR_{25}$, $NR_{26}R_{27}$ or an alkyl, alkenyl, alkynyl cycloalkyl, cycloheteroalkyl, aryl or heteroaryl group each optionally substituted;
each $R_{11}$ is independently H or an alkyl, haloalkyl, alkenyl, or alkynyl group each optionally substituted;
$R_{12}$, $R_{13}$, and $R_{25}$ are each independently H or an alkyl, haloalkyl, alkenyl, alkynyl cycloalkyl or aryl group each optionally substituted;
$R_{26}$ and $R_{27}$ are each independently H, $OR_{11}$, $COR_{12}$, $CO_2R_{13}$ or an alkyl, alkenyl, alkynyl cycloalkyl, cycloheteroalkyl, aryl or heteroaryl group each optionally substituted or $R_{26}$ and $R_{27}$ may be taken together with the atom to which they are attached to form an optionally substituted 5- to 7-membered ring optionally interrupted by an additional heteroatom selected from O, N or S;
or
a tautomer thereof, a stereoisomer thereof or a pharmaceutically acceptable salt thereof.

2. The compound according to claim 1 wherein $R_6$ is H or halogen.

3. The compound according to claim 1 wherein $R_1$ and $R_2$ are H.

4. The compound according to claim 1 wherein $R_3$ is a $C_1$-$C_4$ alkyl group.

5. The compound according to claim 1 wherein $R_7$ is an optionally substituted phenyl or heteroaryl group and is attached in the 7-position.

6. The compound according to claim 5 wherein $R_1$ and $R_2$ are H and $R_3$ is a $C_1$-$C_4$ alkyl group.

7. The compound according to claim 1 selected from the group consisting of:
2'-amino-2-methoxy-1,1'-dimethyl-7-bromo-10,11- dihydrospiro[dibenzo[a,d][7]-annulene-5,4'-imidazol]-5' (1'H)-one;
2'-amino-2-methoxy-1'-methyl-7-bromo-10,11-dihydrospiro[dibenzo[a,d][7]annulene-5,4'-imidazol]-5' (1'H)-one;
2'-amino-2-methoxy-1,1'-dimethyl-7-pyridin-3-yl-10,11-dihydrospiro[dibenzo[a,d][7]annulene -5,4'-imidazol]-5'(1'H)-one;
2'-amino-7-(2-fluoropyridin-3-yl)-2-methoxy-1,1'-dimethyl-10,11-dihydrospiro[dibenzol[a,d][7]annulene-5, 4'-imidazol]-5'(1'H)-one;
2'-amino-2-methoxy-1,1'-dimethyl-7-pyrimidin-5-yl-10, 11-dihydrospiro[dibenzo[a,d][7]annulene -5,4'-imidazol]-5'(1'H)-one;
2'-amino-7-(6-fluoropyridin-3-yl)-2-methoxy-1,1'-dimethyl-10,11-dihydrospiro[dibenzo[a,d][7]annulene-5, 4'-imidazol]-5'(1'H)-one;
2'-amino-7-(2,5-difluorophenyl)-2-methoxy-1,1'-dimethyl -10,11-dihydrospiro[dibenzo[a,d][7]annulene-5, 4'-imidazol]-5'(1'H)-one;
3-(2'-amino-8-methoxy-1',9-dimethyl-5'-oxo-1'5',10,11-tetrahydrospiro[dibenzo[a,d][7]annulene -5,4'-imidazol]-3-yl)benzonitrile;
2'-amino-2-methoxy-7-(3-methoxyphenyl)-1,1'-dimethyl-10,11-dihydrospiro[dibenzo[a,d][7]annulene-5, 4'-imidazol]-5'(1'H)-one;
2'-amino-7-(3,5-difluorophenyl)-2-methoxy-1,1'-dimethyl -10,11-dihydrospiro[dibenzo[a,d][7]annulene-5, 4'-imidazol]-5'(1'H)-one;
(5S)-2'-amino-2-methoxy-1,1'-dimethyl-7-pyrimidin-5-yl-10,11-dihydrospiro[dibenzo[a,d][7]annulene-5,4'-imidazol]-5'(1'H)-one;
(5R)-2'-amino-2-methoxy-1,1'-dimethyl-7-pyrimidin-5-yl-10,11-dihydrospiro[dibenzo[a,d][7]annulene-5,4'-imidazol]-5'(1 'H)-one;
2'-amino-2-methoxy-1'-methyl-7-phenyl-10,11-dihydrospiro[dibenzo[a,d][7]annulene-5,4'-imidazol]-5 (1'H)-one;
a tautomer thereof;
a stereoisomer thereof; and
a pharmaceutically acceptable salt thereof.

8. A pharmaceutical composition which comprises a pharmaceutically acceptable carrier and an effective amount of a compound of formula 1

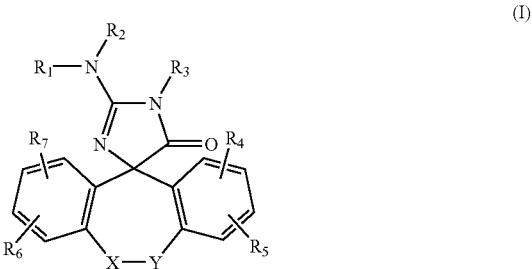

(I)

wherein
- X is $CH_2$;
- Y is $CH_2$;
- $R_1$ and $R_2$ are each independently H, or an optionally substituted alkyl group;
- $R_3$ is H or an alkyl group optionally substituted;
- $R_4$ and $R_5$ are each independently H, halogen, $OR_{11}$ or an alkyl, alkenyl, or alkynyl, group optionally substituted;
- $R_6$ and $R_7$ are each independently H, halogen, CN, $OR_{25}$, $NR_{26}R_{27}$ or an alkyl, alkenyl, alkynyl cycloalkyl, cycloheteroalkyl, aryl or heteroaryl group each optionally substituted;
- each $R_{11}$ is independently H or an alkyl, haloalkyl, alkenyl or alkynyl group each optionally substituted;
- $R_{12}$, $R_{13}$, and $R_{25}$ are each independently H or an alkyl, haloalkyl, alkenyl, alkynyl cycloalkyl or aryl group each optionally substituted;
- $R_{26}$ and $R_{27}$ are each independently H, $OR_{11}$, $COR_{12}$, $CO_2R_{13}$ or an alkyl, alkenyl, alkynyl cycloalkyl, cycloheteroalkyl, aryl or heteroaryl group each optionally substituted or $R_{26}$ and $R_{27}$ may be taken together with the atom to which they are attached to form an optionally substituted 5- to 7-membered ring optionally interrupted by an additional heteroatom selected from O, N or S;

or a tautomer thereof, a stereoisomer thereof or a pharmaceutically acceptable salt thereof.

9. The composition according to claim 8 having a formula I compound wherein $R_1$ and $R_2$ are H and $R_3$ is methyl.

10. The composition according to claim 9 having a formula I compound wherein $R_7$ is an optionally substituted phenyl or heteroaryl group and is attached in the 7-position.

11. The composition according to claim 8 having a formula I compound selected from the group consisting of:

2'-amino-2-methoxy-1,1'-dimethyl-7-bromo-10,11-dihydrospiro[dibenzo[a,d][7]-annulene-5,4'-imidazol]-5'(1'H)-one;

2'-amino-2-methoxy-1'-methyl-7-bromo-10,11-dihydroepiro[dibenzo[a,d][7]annulene-5,4'-imidazol]-5'(1'H)-one;

2'-amino-2-methoxy-1,1'-dimethyl-7-pyridin-3-yl-10,11-dihydrospiro[dibenzo[a,d][7]annulene -5,4'-imidazol]-5'(1'H)-one;

2'-amino-7-(2-fluoropyridin-3-yl)-2-methoxy-1,1'-dimethyl-10,11-dihydrospiro[dibenzo[a,d][7]annulene-5,4'-imidazol]-5'(1'H)-one;

2'-amino-2-methoxy-1,1'-dimethyl-7-pyrimidin-5-yl-10,11-dihydrospiro[dibenzo[a,d][7]annulene -5,4'-imidazol]-5'(1'H)-one;

2'-amino-7-(6-fluoropyridin-3-yl)-2-methoxy-1,1'-dimethyl-10,11-dihydrospiro[dibenzo[a,d][7]annulene-5,4'-imidazol]-5'(1 'H)-one;

2'-amino-7-(2,5-difluorophenyl)-2-methoxy-1,1'-dimethyl -10,11-dihydrospiro[dibenzol[a,d][7]annulene-5,4'-imidazol]-5'(1'H)-one;

3-(2'-amino-8-methoxy-1',9-dimethyl-5'-oxo-1',5',10,11-tetrahydrospiro[dibenzo[a,d][7]annulene -5,4'-imidazol]-3-yl)benzonitrile;

2'-amino-2-methoxy-7-(3-methoxyphenyl)-1,1'-dimethyl-10,11-dlhydrospiro[dibenzo[a,d][7]annulene-5, 4'-imidazol]-5'(1'H)-one;

2'-amino-7-(3,5-difluorophenyl)-2-methoxy-1,1'-dimethyl -10,11-dihydrospiro[dibenzo[a,d][7]annulene-5, 4'-imidazol]-5'(1'H)-one;

(5S)-2'-amino-2-methoxy-1,1'-dimethyl-7-pyrimidin-5-yl-10,11-dihydrospiro[dibenzo[a,d][7]annulene-5,4'-imidazol]-5'(1'H)-one;

(5R)-2'-amino-2-methoxy-1,1'-dimethyl-7-pyrimidin-5-yl-10,11-dihydrospiro[dibenzo[a,d][7]annulene-5,4'-imidazol]-5'(1'H)-one;

2'-amino-2-methoxy-1'-methyl-7-phenyl-10,11-dihydrospiro[dibenzo[a,d][7]annulene-5,4'-imidazol]-5'(1'H)-one;

a tautomer thereof;

a stereoisomer thereof; and a pharmaceutically acceptable salt thereof.

\* \* \* \* \*